(12) United States Patent
Reiss et al.

(10) Patent No.: US 6,583,336 B1
(45) Date of Patent: Jun. 24, 2003

(54) STIMULATION OF HOMOLOGOUS RECOMBINATION IN EUKARYOTIC ORGANISMS OR CELLS BY RECOMBINATION PROMOTING ENZYMES

(75) Inventors: Bernd Reiss, Leverkusen (DE); Hans Kosak, Bonn (DE); Manfred Klemm, Pullheim (DE); Jeff Schell, Köln (DE)

(73) Assignee: BASF Plant Science GmbH, Ludwigshafen (DE)

( * ) Notice: Subject to any disclaimer, the term of this patent is extended or adjusted under 35 U.S.C. 154(b) by 0 days.

(21) Appl. No.: 09/029,228

(22) PCT Filed: Aug. 30, 1996

(86) PCT No.: PCT/EP96/03824

§ 371 (c)(1),
(2), (4) Date: Apr. 28, 1998

(87) PCT Pub. No.: WO97/08331

PCT Pub. Date: Mar. 6, 1997

(30) Foreign Application Priority Data

Aug. 30, 1995 (EP) .............................. 95113644
Aug. 31, 1995 (EP) .............................. 95113691

(51) Int. Cl.[7] ........................ C12N 15/82; C12N 15/84; C12N 15/31; C12N 5/04; A01H 5/00
(52) U.S. Cl. ...................... 800/278; 800/288; 800/292; 800/293; 800/294; 800/306; 800/317.3; 435/69.8; 435/320.1; 435/419; 435/468; 435/469; 435/470
(58) Field of Search .............................. 435/69.1, 70.1, 435/71.1, 468, 471, 410, 418, 419, 420, 252.3, 320.1, 69.8, 469, 470; 536/23.1, 23.7; 800/278, 290, 295, 288, 292, 293, 306, 294, 317.3

(56) References Cited

PUBLICATIONS

Boase et al. In Vitro Cellular and Developmental Biology. 1998. vol. 34: 46–51.*
Paszkowski et al. EMBO J. 1988. vol. 7: 4021–4026.*
Sancar et al. Proc. Natl. Acad. Sc. 1980. vol. 77: 11–15.*
West et al. Proc. Natl. Acad. Sci. 1981. vol. 78: 100–104.*
Menetski et al. J. Mol. Biol. 211: 845–855, 1990.*
Cerutti et al. Mol. Cell. Biol. 15(6): 3003–3011, Jun. 1995.*
Spivack et al. Mutation Research 246: 103–107, 1991.*
Kido et al. Exp. Cell. Res. 198(1): 107–114, 1992.*
Shcherbakova, Olga G. et al., "Overexpression of bacterial RecA protein . . . ," Mutation Research 459 (2000), pp. 65–71.
Lanzov, Vladislav A., "Gene targeting for gene therapy: prospects," Molecular Genetics and Metabolism 68 (1999), pp. 276–282.
Yanez et al., "Gene targeting is enhanced in human cells . . . ," Gene Therapy 6 (1999), pp. 1282–1290.
Dunderdale, HJ et al., Recombination genes and proteins, Current Opinion in Genetics & Development (1994), 4(2): 221–8.
Shinohara, A et al., Rad51/RecA protein families and the associated . . . , Mutation Research (1999), 435: 13–21.
Thacker, J. et al., A surfeit of RAD51–like genes?, Trends in Genetics (1999), 15(5): 166–168.
Vasquez, KM. et al., Manipulating the mammalian . . . , Proc Natl Acad Sci USA (2001), 98(15): 8403–10. Review.

* cited by examiner

*Primary Examiner*—David T. Fox
(74) *Attorney, Agent, or Firm*—Birch, Stewart, Kolasch & Birch, LLP

(57) ABSTRACT

The present invention relates to a novel process for the production of transgenic organisms or transgenic cells, to transgenic orgaisms or transgenic cells obtainable by the process of the present invention, to the use of vectors comprising DNA encoding a recombination promoting enzymes for curing impairments caused by environmental influences in plants or plant cells and for gene therapy in mammals or mammalian cells, and to novel vectors.

20 Claims, 8 Drawing Sheets

1: 30min  2: 20min  3: 10min
4: 0min   5: Marker 1
6: 30min −SSB −ATP
7: 30min −SSB
8: 30min −Mg
9: 30min −ATP
10: 30min −(nt)−RecA
11: 0min −(nt)RecA
12: Marker 1  13: Marker 2

DAPI  Anti-RecA

SEQUENCE LISTING

```
<160> NUMBER OF SEQ ID NOS: 8

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence:
      amino-terminal part of recA without its initiation codon and two
      complementary oligonucleotides

<400> SEQUENCE: 1
ggggactcct cctaagaaga agcgtaaggt tatggcgat                              39

<210> SEQ ID NO 2
<211> LENGTH: 41
<212> TYPE: DNA
<213> ORGANISM: Artificial Sequence
<220> FEATURE:
<223> OTHER INFORMATION: Description of Artificial Sequence: portion of
      recA and SV40 nuclear localization sequence

<400> SEQUENCE: 2
cgatcgccat aaccttacgc ttcttcttag gaggagtccc c                          41

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: primer
      homologous to the -90 region of the 35S promoter

<400> SEQUENCE: 3
gtggattagt gtgatatctc c                                                21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: primer
      homologous to the sequence of the nptII gene

<400> SEQUENCE: 4
ccgctcagaa gaactcgtca                                                  20
```

```
<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: nuclear
      targeting sequence

<400> SEQUENCE: 5
atggcttcta tgatggggac tcctcctaag aagaagcgta aggtt              45

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: nuclear
      targeting sequence

<400> SEQUENCE: 6

Met Ala Ser Met Met Gly Thr Pro Pro Lys Lys Lys Arg Lys Val
 1               5                  10                  15

<210> SEQ ID NO 7
<211> LENGTH: 51
<212> TYPE: DNA
<213> ORGANISM: Artificial Sequence
<220> FEATURE:
<223> OTHER INFORMATION: Description of Artificial Sequence: artificial
      ribosome binding site

<400> SEQUENCE: 7
atgaatgaat tcggatcccc ggggactcct cctaagaaga agcgtaaggt t         51

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: artificial
      ribosome binding site

<400> SEQUENCE: 8

Met Asn Glu Phe Gly Ser Pro Gly Thr Pro Pro Lys Lys Lys Arg Lys
 1               5                  10                  15
Val
```

STIMULATION OF HOMOLOGOUS RECOMBINATION IN EUKARYOTIC ORGANISMS OR CELLS BY RECOMBINATION PROMOTING ENZYMES

This application is the national phase under 35 U.S.C. § 371 of prior PCT International Application No. PCT/EP96/03824 which has an International filing date of Aug. 30, 1996 which designated the United States of America, the entire contents of which are hereby incorporated by reference.

FIELD OF THE INVENTION

The present invention relates to a novel process for the production of transgenic organisms or transgenic cells, to transgenic organisms or transgenic cells obtainable by the process of the present invention, to the use of vectors comprising DNA encoding a recombination promoting enzymes for curing impairments caused by environmental influences in plants or plant cells and for gene therapy in mammals or mammalian cells, and to novel vectors.

The process of homologous recombination requires search for homology, recognition of sequence similarity, and strand exchange between two DNA molecules. In bacteria, these different steps are mediated by a single protein, the RecA protein (for review see:Roca and Cox, 1990), which plays a central role in the recombination pathway of *E. coli*. However, additional proteins are needed to initiate recombination and to resolve the intermediates created by RecA. Recombination is initiated by the generation of single-stranded DNA (ssDNA) and DNA ends in *E. coli* and presumably in all organisms. In *E. coli*, the combined action of the products of the recB, recC, and recD genes initiates a major recombination pathway (for review see: Dunderdale and West, 1994). ssDNA is recognised by RecA protein and double-stranded DNA (dsDNA) is actively searched for. Exchange of complementary strands leads to the formation of recombination intermediates (Holliday structures). The intermediates can be resolved by different pathways; the major one involves the action of the RuvA, RuvB, and RuvC proteins. All of the recombination proteins have to work in concert to complete recombination successfully. Proteins remarkably similar to RecA have been found in a number of eukaryotic cells such as budding yeast, fission yeast, humans, mice, chicken, and plants (Terasawa et al., 1995; for review see: Kowalczykowski and Eggleston, 1994). The best characterised ones are the Dmc1 and Rad51 proteins from Saccharomyces cerevisiae. In both cases the corresponding genes are essential for recombination and the proteins show considerable sequence homology to RecA. A comparison of the primary sequences of Dmc1 and several bacterial RecA proteins suggests that these proteins evolved from a single progenitor before the separation of prokaryotes and eukaryotes. In addition, Rad51 was shown to be structurally very similar to RecA. Rad51 forms DNA/protein filaments, strikingly similar in tertiary structure to those formed with RecA (Ogawa et al., 1993). While previous studies failed to show ATP-dependent homologous pairing and strand-exchange mediated by Rad51 (Shinohara, et al., 1992; Ogawa et al., 1993), more recent experiments have demonstrated these activities (Sung, 1994). Rad51 interacts with other proteins, e.g. Rad52 and Dmc1, so Rad51 may be part of a complex involved in recombination.

However, the complexity of these proteins strongly argues against their being simply a homologue as equivalent to the *E.coli* RecA protein. Accordingly, different modes of biological activity may be expected.

Various reports have been published focusing on the activity of *E. coli* RecA protein in animal and in particular in mammalian cells. Thus, Kido et. al, 1992 report on the introduction of functional bacterial RecA protein which was fused to the nuclear location signal of SV40 large T-antigen into mammalian cells. However, no functional studies of the introduced protein were carried out. WO 93/22443 deals with the targeting of exogenous polynucleotide sequences coated on *E. coli* RecA protein to chromosomal DNA of mammalian cells. This document shows that RecA protein coated oligonucleotides can efficently be targeted to correct chromosomal positions, RecA can stimulate extrachromosomal recombination, and RecA short DNA complexes can be used for gene targeting in mammalian cells. However, the authors failed to show stimulation of homologous recombination in living cells or an entire organism. Spivak et. al (1991) report the increased survival of HeLa cells upon treatment with RecA protein containing liposomes after irradiation. However, RecA stimulated survival was only marginal. Cerruti et al. report on the recombinatorial activity of *E.coli* RecA protein in plastids which, however, had no effect on DNA repair or cell survival, probably due to the fact that plastids have an own recombination promoting enzyme which is homologous to *E.coli* RecA. Thus, so far successful experiments with the goal of targeting RecA protein to eukaryotic nuclei which yield a significantly high recombinatorial activity to allow for the industrial applicability of such processes have not been carried out. For example, as regards plant cells, introduction of RecA/DNA complexes, in analogy to WO93/22443, in plant cells by PEG-mediated transformation turned out to be extremely difficult. These complexes exhibit an apparent toxicity and lead to cell death of nearly the total protoplast population. Also, Kido et. al, loc. cit., had reported on the failure to introduce RecA protein into the nuclei of mammalian cells. Therefore, in view of the prior art investigations it was highly questionable as to whether a recombination promoting enzyme such as RecA could be functionally introduced into the nuclei of eukaryotic cells and, furthermore, whether such an introduced RecA protein would indeed be able to enter the cell nucleus and actively promote recombination to an industrially applicable extent.

SUMMARY OF THE INVENTION

Thus, the technical problem underlying the present invention was to provide a process for the production of a transgenic organism or a transgenic cell, said process making use of a recombination promoting enzyme. The solution to said technical problem is provided by the embodiments characterised in the claims. Accordingly, the present invention relates to a process for the production of a transgenic organism or a transgenic cell comprising (a) insertion (aa) of a DNA into the genome of an organism or a cell, said DNA comprising a DNA which (aaa) confers to the transgenic organism or the transgenic cell one or more desired characteristics; which (aab) additionally encodes at least one selection marker expressible in said organism or said cell; and which (aac) optionally encodes a recombination promoting enzyme or an enzymatically active derivative or part thereof, wherein the recombination promoting enzyme or the enzymatically active part thereof confers the or one of the desired characteristics; or, if (aac) does not apply, (ab) of a recombination promoting enzyme or an enzymatically active derivative or part thereof in combination with said DNA (aa), into an organism or a cell;

(b) selection of transgenic organisms or cells, which have taken up said DNA or said DNA and said protein according to (a); and (c) culturing of the desired transgenic organism or the desired transgenic cell in a suitable culture medium.

Thus, it is conceivable in accordance with the present invention that the recombination promoting enzyme confers the desired characteristic or is one of the desired characteristics. In the first instance, the method of the invention may yield, for example, plants with a hyperrecombinant phenotype which might be of use in plant breeding, plants more tolerant to environmental influences, for example, caused by UV or ozone, or plants more tolerant to DNA damage. In the second case, the recombination promoting enzyme may be used to introduce by promoting recombination a DNA sequence of interest into the genome of a cell or an organism. These transgenics are expected to improve the frequency of gene targeting and make this methodology applicable, for example, for plant breeding.

Further, the recombination promoting enzyme may be introduced into the cell or organism as encoded by a corresponding nucleotide sequence which, upon expression, yields said recombination promoting enzyme. Alternatively, the recombination promoting enzyme may be introduced into said cell or organism as such. In this case, the DNA to be inserted encodes a protein with the second or further desired characteristic. The nucleotide sequence encoding the second or further desired characteristics may then be introduced into the genome of said cell or organism by the activity of the recombination promoting enzyme, which, naturally, has to be biologically active in said cell or organism. For example, the second or further characteristic may be an additional protein to be expressed in said cell or organism or, it may be a DNA sequence that, upon recombination into the genome of said organism or said cell, results in the disruption of a naturally occurring or a transgenic gene function. This approach also allows the expression of modified proteins without interference endogenous non-modified copies and allows to circumvent intertransformant variation. It is also expected that problems arising from instable expression and gene silencing can be circumvented using gene targeting in plants.

For testing the efficacy of the process of the invention, a reproducible and quantitative assay for mitomycin C resistance was developed on the basis of the data and systems published by Lebel et al. (1993). Mitomycin C is known to intercalate in vivo into DNA leading to cross-linking of complementary strands (Borowy-Borowski et al., 1990). Cross-linking leads to inhibition of DNA synthesis in bacteria without concomitant effect on RNA or protein synthesis (Iyer and Szybalski, 1963). In Ustilago maydis and Saccharomyces cerevisiae, mitomycin C was shown to stimulate homologous recombination without being mutagenic (Holliday, 1964). Similar observations were also made in different higher eukaryotic cells (Suzuki, 1965; Shaw and Cohen, 1964; Wang et al., 1988). The data indicate that mitomycin C efficiently blocks DNA replication. The resultant daughter-strand blocks are thought to be repaired in many organisms by homologous recombination (sister-chromatid exchange) and excision repair. Lebel et al. (1993) showed that mitomycin C stimulates intrachromosomal recombination in plant cells, thus pointing to recombinational repair of mitomycin C lesions in plants.

In accordance with the present invention it was found that high mitomycin C concentrations kill untreated plant cells as a representative of eukaryotic cells efficiently, presumably because the capacity of the endogenous repair/recombination system is exhausted. Thus it was further found for the wild-type that protoplast survival under mitomycin C treatment followed a dose-response curve similar to those frequently seen with bacteria and yeast: a shoulder at low doses and a semi-logarithmic decrease at higher doses (FIG. 7). Evaluation of the dose-response curves (FIG. 7) as described by Friedberg (1985) suggests that nt-RecA expression obtained in accordance with the process of the present invention provides the cells with the capacity to repair damage caused by up to 50 $\mu$g/ml mitomycin C whereas the endogenous repair mechanism in wild-type tobacco protoplasts can only repair damage caused by up to 15 $\mu$/ml of mitomycin C.

Thus, plant cells expressing nt-RecA exhibited a considerably higher resistance to this drug. This suggests that RecA can function in plant cells, interacting with or supplementing the endogenous plant recombination machinery. Furthermore, RecA directly stimulated intrachromosomal recombination in plants. On the basis of this data it may be expected that the process of the present invention yields much higher recombination frequencies than any of the processes described by the prior art.

Although the present invention has been illustrated only with regard to plant cells, the teachings disclosed herein apply as well to other eukaryotic cells such as mammalian cells. It is expected that the present invention allows, for the first time, for a recombination efficiency in the nuclei of eukaryotic cells or organisms that leads to an industrially applicable process for the generation of such transgenic cells or organisms.

In a preferred embodiment of the process of the invention, said transgenic organism or transgenic cell is a plant or a plant cell.

In a most preferred process of the present invention said plant or plant cells is or is derived from *Nicotiana tabacum* or *Arabidopsis thaliana*.

A further preferred embodiment of the invention relates to a method wherein said transgenic organism as transgenic cell is a mammal or a mammalian cell, a fungus, a yeast or a bacterium.

In a further preferred process said desired characteristics are stimulation of homologous recombination, enhancement of gene targeting, stimulation of endogenous mechanisms for repair of DNA damage, thus leading to tolerance to various chemical and physical agents (ozone, UV). Additionally, said further desired characteristic may, for example, be an additional protein expressed, which alters the phenotype of the transgenic organism or cell in a desired way such as the expression of additional surface markers or the expression of different/additional metabolic enzymes. Further, said characteristic may lead to the disruption of a naturally occurring gene function in said organism or said cell.

In another preferred process said selection marker is $Hyg^R$, $Km^R$, $PPT^R$, $Mtx^R$ or $Sul^R$.

The person skilled in the art is well familiar with these selection markers, where $Hyg^R$ stands for hygromycin resistance, $Km^R$ stands for Kanamycin resistance, $PPT^R$ stands for phosphonotricin (BASTA) resistance, $Mtx^R$ stands for methotrexate resistance and $Sul^R$ stands for sulfonamide resistance. The person skilled in the art is, however, able to replace these preferred selection markers by any other one suitable in the process of the invention.

In an additional preferred embodiment of the process of the invention, said recombination promoting enzyme is the *E.coli* RecA protein.

In a further preferred process of the present invention said derivative of said recombination promoting enzyme is a fusion protein of the *E.coli* RecA protein and a nuclear targeting sequence.

The experimental data obtained in accordance with this preferred embodiment showed that nt-RecA was able to increase the UV resistance of recA *E. coli*. The chimeric protein was capable of binding to ssDNA and to catalyse strand-exchange in vitro about as efficiently as RecA. Interestingly, unlike RecA, nt-RecA showed a high ATPase activity in the absence of ssDNA. This ssDNA-independent activity of nt-RecA was stimulated by addition of ssDNA by the same incremental amount as RecA itself. It is presently not known whether these activities result from two different proteins (nt-RecA and a RecA-like degradation product) in the preparation, or is an intrinsic property of nt-RecA. It can also not be totally excluded that ATPase activity of nt-RecA in the absence of ssDNA is due to trace amounts of contaminating ATPase or DNA, which may have escaped detection by gel electrophoresis and staining. However, it is likely that the nt-RecA fusion protein indeed has different ATPase properties. Since the level of ATPase of nt-RecA in the absence of ssDNA is somewhat higher than that of RecA in the presence of ssDNA one might think of nt-RecA as a modified RecA protein which is constitutively activated in a manner which is reminiscent of the RecA441 and RecA730 proteins (Witkin et al., 1982). ATPase activity of RecA seems to serve two different functions: recycling of the enzyme and overcoming nonhomologous regions of DNA (For review see: Kowalczykowski and Eggelston, 1994; Roca and Cox, 1990).

In a most preferred embodiment said nuclear targeting sequence is the T SV40 nuclear targeting sequence.

The SV40 nuclear targeting sequence is well known in the art and need not be described here any further.

In a still further preferred embodiment of the present invention said insertion is mediated via PEG transformation, Agrobacterium transformation, electroporation, particle bombardment, liposome fusion, in planta transformation, calcium phosphate precipitation, or virus infection.

The optimal process employed depends on the taxonomic origin of the organism or cell to be transfected. The person skilled in the art is well aware of which insertion method is best suited to this purpose.

The invention further relates to a transgenic organism or a transgenic cell obtainable by the process of the invention.

Additionally, the invention relates to a vector comprising a DNA encoding a nuclear targeting sequence operatively linked to a DNA encoding a recombination promoting enzyme or an enzymatically active part thereof, at least one selection marker, and, optionally, at least one further DNA encoding a desired characteristic, wherein the nuclear targeting sequence/recombination promoting enzyme fusion protein encoded by said vector has ATPase activity.

Surprisingly, it was found in accordance with the present invention that the nuclear targeting sequence/recombination promoting enzyme fusion protein as exemplified by the fusion protein wherein the nuclear targeting sequence is derived from SV40 and the recombination promoting enzyme is the *E.coli* RecA protein confers a high ATPase activity. Said activity appears to serve two different functions: First, it appears to recycle the enzyme and secondly, it appears to overcome non-homologous regions of DNA.

The at least one selection marker comprised in said vector which is capable of expressing the various DNA sequences comprised therein, have been already discussed herein above. The same holds true for the further DNAs encoding a desired characteristic which may also be comprised in the vector of the invention.

In a preferred embodiment of said vector, said nuclear targeting sequence is the T SV40 nuclear targeting sequence. Additionally or alternatively, the recombination promoting enzyme is the *E.coli* RecA protein.

In a most preferred embodiment said vector of the invention is pS/nt-RecA or pEV/nt-RecA. The construction of said vectors is amply described in Example 1. Further details of said vectors are given in FIG. 1.

Further, the invention relates to the use of a vector of the invention or a vector comprising a DNA which confers to a cell to be transformed or transfected therewith one or more desired characteristics; said DNA additionally encoding at least one selection marker expressible in said cell and further encoding a recombination promoting enzyme or an enzymatically active derivative or part thereof, wherein the recombination promoting enzyme or the enzymatically active part thereof confers the or one of the desired characteristics, for curing impairments caused by environmental influences in plants or plants cells. As regards the selection markers, recombination promoting enzymes and insertion processes, preferred embodiments thereof have been described herein above.

In a preferred embodiment of said use, said impairments are caused by damage to DNA, preferably by UV irradiation, ozone, $SO_2$, methylating agents or mutagenic agents.

In a final preferred embodiment of the invention, the vector described herein above is used for gene therapy in mammals or mammalian cells. Such methods for gene therapy are amply discussed in the art so that the technical details are known to or derivable without further ado by the person skilled in the art.

Figure 1:
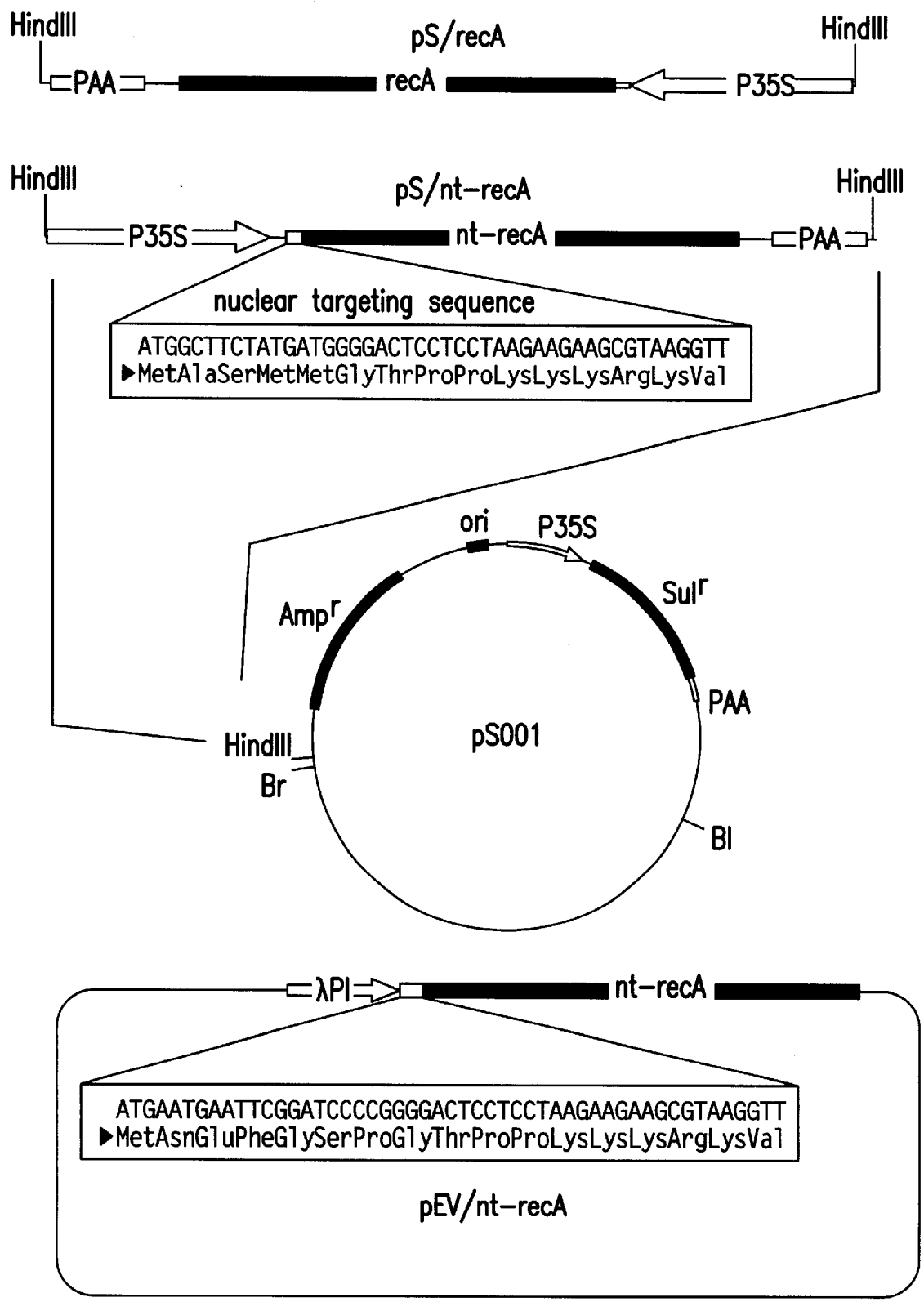
FIG. 1: SCHEMATIC REPRESENTATION OF TRANSGENIC RECA GENES.

Coding sequences are indicated by solid bars. In recA transgenes, open boxes indicate sequences which were added to the recA coding region. Small boxes indicate sequences not coding for proteins. The nucleotide sequences and corresponding amino acid sequences which was added to make pS/nt-recA and pEV/nt-recA are indicated. Promoters are shown as open arrows, polyadenylation signals as open boxes. Abbreviations: HindIII, recognition sequence for HindIII endonuclease; P35S, CaMV 35S promoter; PAA, polyadenylation signal from CaMV; ori, *E. coli* origin of replication; Sul$^r$, sulfonamide resistance gene, Amp$^r$, ampicillin resistance gene; Br, T-DNA right border sequence; Bl, T-DNA left border sequence; $\lambda P_l$, leftward promoter of phage lambda.

FIG. 2: COMPARISON OF ATPASE ACTIVITIES OF RECA AND NT-RECA.

RecA and nt-RecA proteins (100 pMol) were respectively incubated with radioactively labeled ATP in the presence or absence of ssDNA. The ATP turnover was determined and specific activities calculated.

FIG. 3: COMPARISON OF SINGLE-STRAND BINDING ACTIVITIES OF RECA AND NT-RECA.

0, 20, 50, and 100 pMol of RecA and nt-RecA protein respectively, were incubated with 400 pMol (nucleotides) of ssDNA in the presence of γSATP. Reaction mixtures were analysed by electrophoresis on 0.8% agarose gels at 4° C. and the DNA stained with ethidium bromide. Where indicated (+deprot.), samples were deproteinised prior to electrophoresis. Marker: Phage lambda DNA digested with PstI endonuclease. The position of the single-stranded substrate DNA in the gel is indicated (ssDNA).

FIG. 4: COMPARISON OF STRAND-EXCHANGE ACTIVITIES OF RECA AND NT-RECA.

RecA and nt-RecA proteins were incubated as described by Menetski et al. (1990), with mixtures of linear double-stranded and circular ssDNA in the presence of single-strand binding protein (SSB) and γSATP, for the time interval indicated in the figure. The mixture was analysed by electrophoresis on 0.8% agarose gel at room temperature and the DNA stained with ethidium bromide. Control reactions which contained no RecA or nt-RecA protein (-(nt)RecA), no ySATP (-ATP), no magnesium (-Mg), no single-strand binding protein (-SSB), or no single-strand binding protein and γSATP(-SSB -ATP) were included. Marker M1 was phage lambda DNA digested with PstI endonuclease, marker M2 was a mixture of relaxed (open circle, oc), linearised (lin), supercoiled (closed coiled circle, ccc) double-stranded and circular single-stranded (ss) DNA. The position of the open circle, the reaction product of the strand-exchange reaction visible in the gel, is indicated by an arrow.

FIG. 5: TRANSGENIC PLANTS EXPRESS RECA AND NT-RECA, RESPECTIVELY.

Proteins separated by electrophoresis on 12% polyacrylamide gels containing SDS were blotted to nitrocellulose, and RecA antigen detected with monoclonal anti-RecA antibody ARM414 (Ikeda et al, 1990). The position of RecA purified from *E. coli* is indicated. Molecular weights were deduced from a mixture of pre-stained proteins (BioRad) which were coelectrophoresed.

Figure 6:
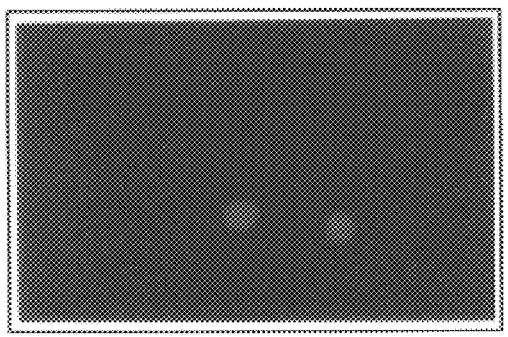
Figure 6:
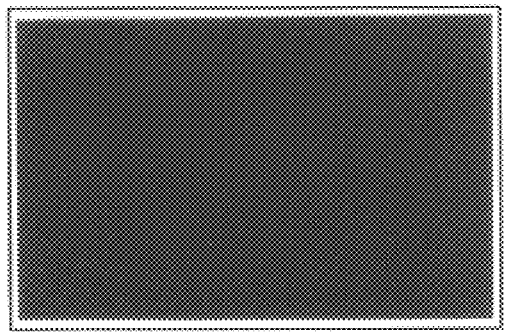
Figure 6:
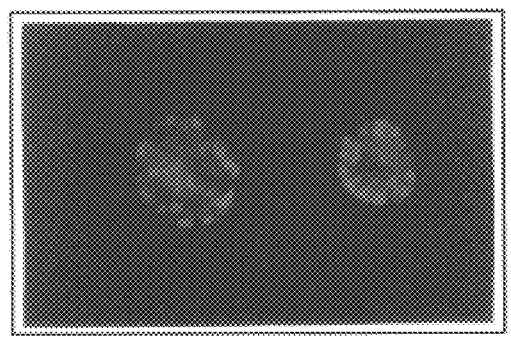
Figure 6:
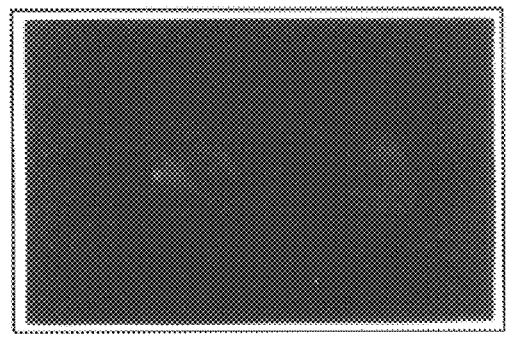
Figure 6:
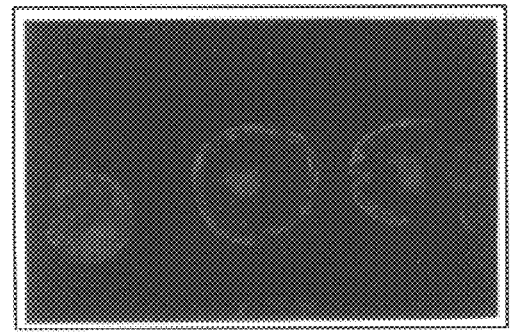
Figure 6:
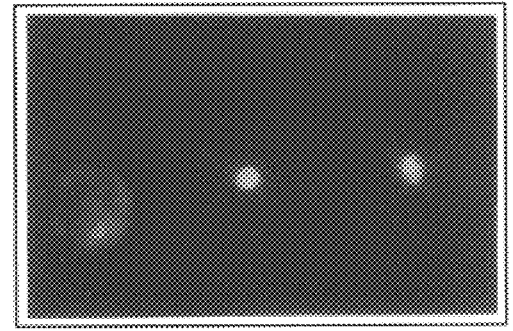

FIG. 6: SUBCELLULAR LOCALISATION OF RECA AND NT-RECA IN TRANSGENIC TOBACCO PLANTS.

Protoplasts were prepared from leaves and the proteins fixed by formaldehyde. Nuclei were visualised by DAPI staining (DAPI panels). The same protoplasts were stained with anti-RecA antibody ARM414 and a FITC-labelled second antibody to visualise RecA antigen (Anti-RecA panels). A: protoplasts from non-transgenic SR1 plants. B: protoplasts from G64/2 plants expressing RecA. C.: protoplasts of G63/19 plants expressing nt-RecA.

Figure 7:
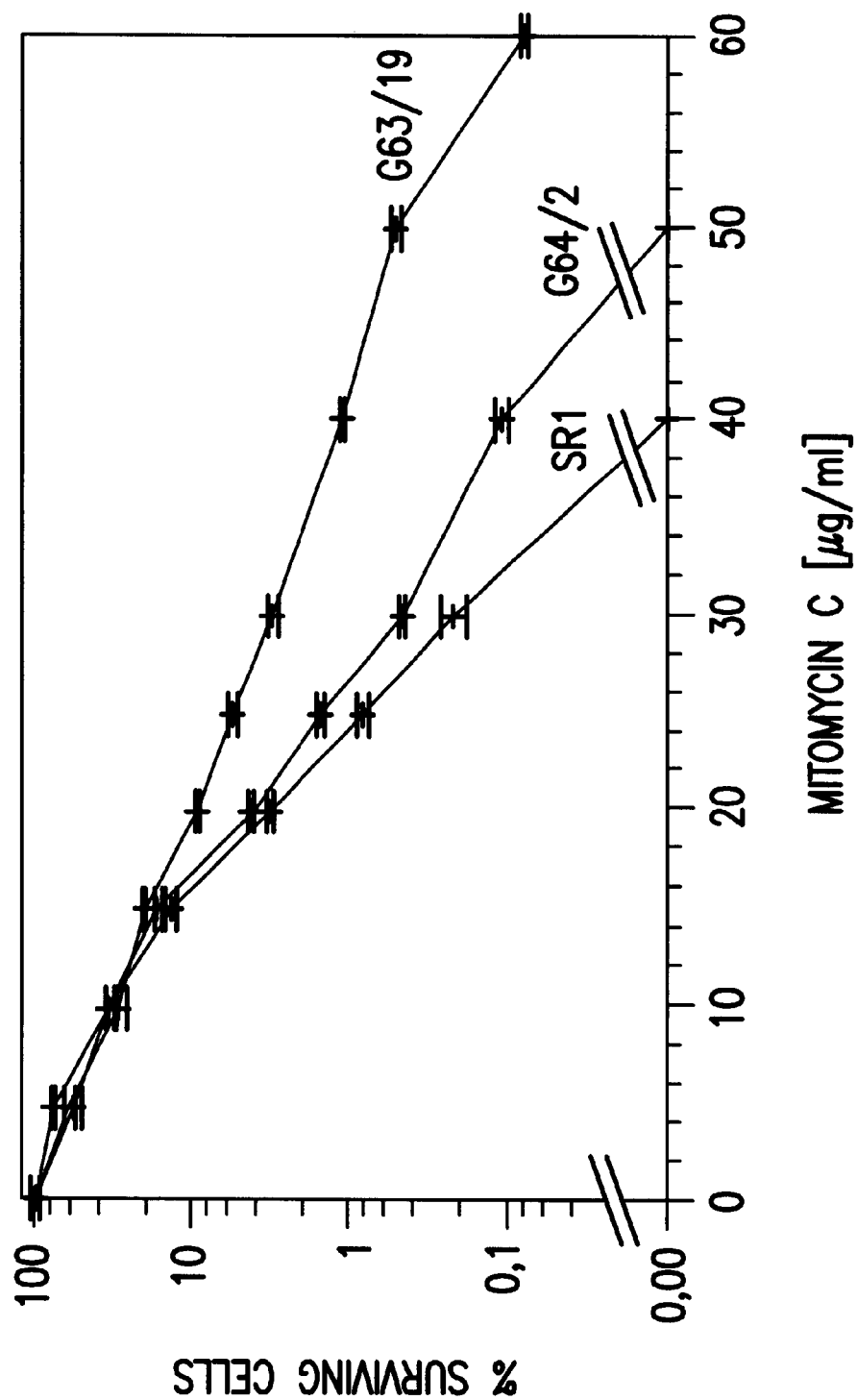

FIG. 7: RECA AND NT-RECA TRANSGENIC PROTOPLASTS ARE MORE RESISTANT TO THE TOXIC EFFECT OF MITOMYCIN C.

Protoplasts obtained from SR1, G64/2, and G63/19 plants were regenerated to microcalli in the presence or absence of mitomycin C. Survival frequencies are defined by the number of microcalli regenerated in the presence of mitomycin C divided by the number of microcalli regenerated in its absence. Mean values obtained from three different data sets are shown. The error bars represent standard deviations calculated for each data point. Data points were reproduced within ±25% for 0, 10, 25, and 50 µ/ml mitomycin C in three additional, independent experiments.

Figure 8:
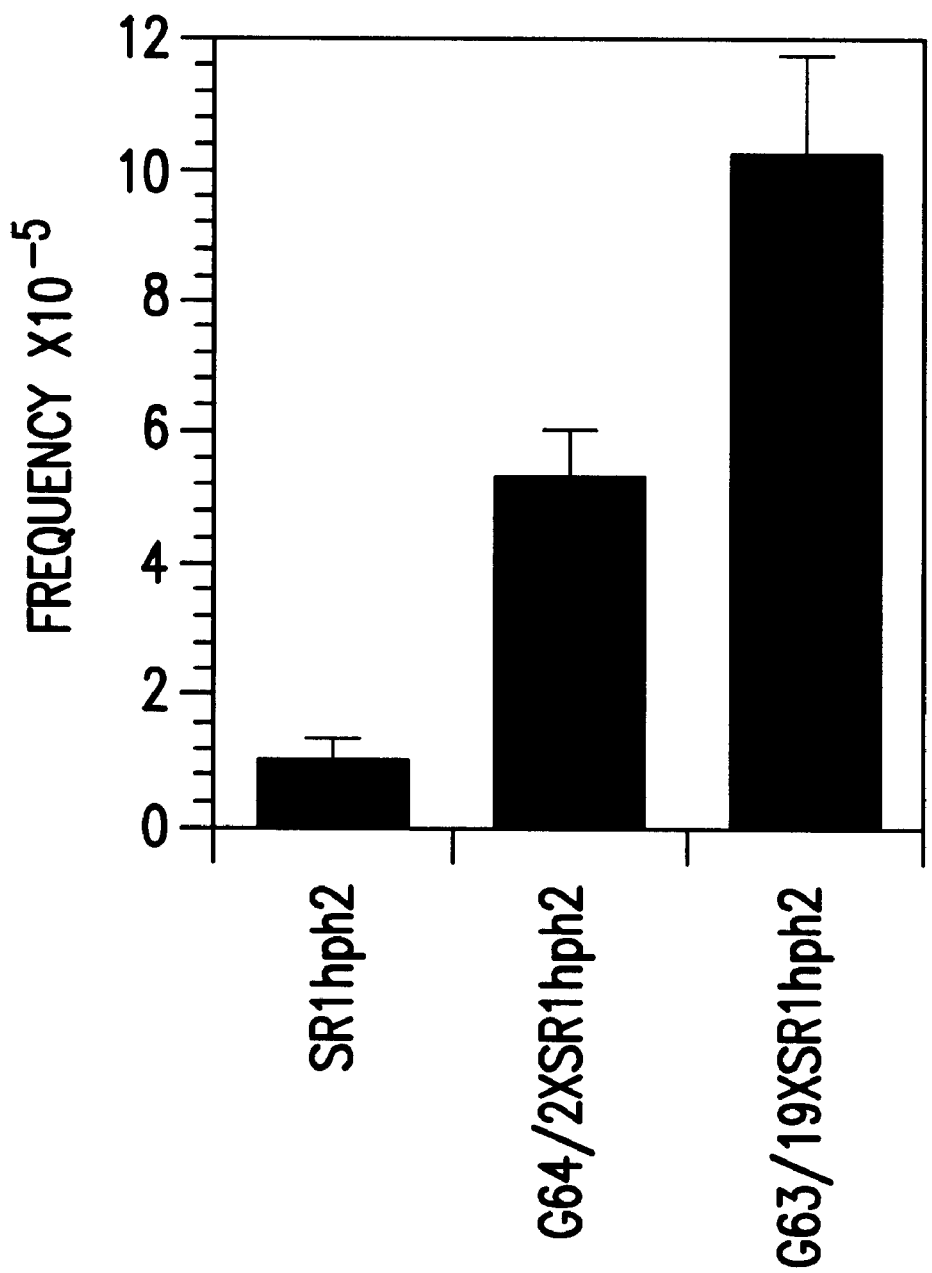

FIG. 8: RECA AND NT-RECA EXPRESSION LEADS TO A STIMULATION OF INTRACHROMOSOMAL RECOMBINATION.

At least $5 \times 10^6$ protoplasts, prepared from each of the 3 lines, were regenerated in the presence of kanamycin in three independent experiments. The frequency of intrachromosomal recombination was calculated from the number of calli growing in the presence of kanamycin, divided by the regeneration frequency obtained in each experiment. Mean values are shown and error bars represent standard deviations.

DETAILED DESCRIPTION OF THE INVENTION

EXAMPLE 1

EXPRESSION AND NUCLEAR TARGETING OF RECA IN PLANTS

Nuclear proteins concentrate in the nucleus irrespective of their size. "Nuclear localisation signals", short stretches of amino acids, are believed to be responsible for targeting of nuclear proteins (for reviews see Dingwall and Laskey, 1986; Silver, 1991). The size of the *E. coli* RecA monomer is close to the exclusion limit of eukaryotic nuclear pores; cytoplasmic ssDNA/RecA filaments would most probably be excluded. RecA protein is unlikely to contain nuclear localisation signals and therefore might be excluded from the nucleus and hence from its target. In order to cover this eventuality RecA protein was expressed in plants as an example of a eukaryotic organism not only in its authentic form but also fused to a nuclear localisation signal.

First the recA gene was modified to remove most bacterial sequences from its up- and downstream untranslated regions. In a second step, the coding sequence was attached 5' to the nuclear localisation sequence of the SV40 large T-antigen (Kalderon et al., 1984) yielding a fusion protein (nt-RecA). To optimise nt-RecA translation, a leader sequence derived from the Rubisco SSU gene (Cashmore, 1983) encoding a translation initiation codon was fused 5' to the nt-RecA coding sequence. Both recA and nt-recA sequences were placed under transcriptional control of the Cauliflower Mosaic Virus (CaMV) 35S promoter and supplied 3' with a eukaryotic polyadenylation signal (FIG. 1). Finally, the genes were inserted into a binary vector suitable for Agrobacterium-mediated plant transformation using a sulfonamide resistance gene ($Sul^r$) to select transformed plants (FIG. 1). In plasmid pS/recA the orientation of the recA transgene relative to the $Sul^r$ gene was such that both genes are transcribed in opposite directions.

In plasmid pS/nt-recA the nt-recA and the $Sul^r$ genes, however, are transcribed in the same direction.

For biochemical characterisation, the nt-RecA fusion protein was also expressed in *E. coli*. For this purpose plasmid pEV/nt-recA was constructed in which nt-recA was fused to an artificial ribosome binding site (FIG. 1).

The experimental details were as follows:

Modified recA genes were derived from plasmid pDR1453 (Sancar and Rupp, 1979). The plasmid was digested with the restriction enzyme SacII, the ends made blunt with DNA Polymerase I large fragment and the amino-terminal part of the recA gene subcloned as a SacII/EcoRI fragment in plasmid pUC18, which had been cut with EcoRI and SmaI yielding plasmid pRecA-1. The same plasmid was digested with HinfI, the ends rendered blunt and the carboxy-terminal part of the recA gene subcloned into pUC19 (EcoRI/SmaI) as a HinfI/EcoRI fragment (pRecA-2). The amino-terminal part was further modified. A BstXI/EcoRI and a TaqI/BstXI fragment obtained from pRecA-1 encoding the amino-terminal part of recA without its initiation codon and two complementary oligonucleotides (5'GGG GAC TCC TCC TAA GAA GAA GCG TAA GGT TAT GGC GAT3' (SEQ ID NO: 1) and 5'CGA TCG CCA TAA CCT TAC GCT TCT TCT TAG GAG GAG TCC CC3' (SEQ ID NO: 2)) encoding the missing codons as well as the SV40 nuclear localisation sequence were inserted into plasmid pUC18 which was had been digested with EcoRI and SmaI, yielding plasmid pRecA-3. The DNA sequence of relevant junctions confirmed the expected structures of the constructs.

For expression of nt-RecA in plants, the leader sequence and the codons encoding the first 4 amino acids of the Rubisco SSU gene were fused to the recA gene. Plasmid pSP64/TPNPTII (Wassmann et al., 1986) contains the amino-terminal part of the SSU gene. This plasmid was digested with EcoRV and SalI and a SmaI/EcoRI fragment derived from pRecA-3 carrying the amino-terminal portion of the recA gene and a EcoRI/SalI fragment from pRecA-2 containing the carboxy-terminal portion inserted to it to yield pRecA-4. The complete nt-recA gene was excised from pRecA-4 by digestion with HindIII and SalI. The HindIII ends were made blunt and the fragment inserted into plasmid pDH51 (Pietrzak et al., 1986), which had been modified to contain an additional HindIII site upstream of the unique EcoRI site. This step fused the CaMV 35S promoter and the polyadenylation signal, respectively, to the nt-recA gene. For expression of RecA in plants, the SmaI/EcoRI fragment from pRecA-3 carrying the amino-terminal portion of the recA gene and the EcoRI/SalI fragment from pRecA-2 containing the carboxy-terminal portion were inserted into the modified pDH51 plasmid via corresponding sites. To obtain plasmid pEV/nt-recA for expression in *E. coli*, the BamHI/EcoRI fragment from pRecA-3 carrying the amino-terminal portion of the recA gene and the EcoRI/SalI fragment from pRecA-2 containing its carboxy-terminal portion were inserted into plasmid pEVvfr1 (Crowl et al., 1985).

The binary vector carrying a Sul$^r$ selectable marker gene was constructed as follows: Plasmid pJIT119 (Guerineau et al., 1990) was digested with HindIII, the ends filled in with DNA polymerase I large fragment, and the HindIII/SalI fragment carrying the Sul$^r$ gene inserted into plasmid pDH51, which had been digested with SmaI and SalI. To obtain pS001, the Sul$^r$ gene fused to the CaMV 35S promoter and polyadenylation signal was exchanged for the methotrexate resistance gene in pM001 (Reiss et al., 1994) via the NcoI and SstI sites. The recA and nt-recA gene, respectively, was exised by digestion with HindIII and was inserted into the unique HindIII site of plasmid pS001 leading to plasmids pS/recA and pS/nt-recA.

EXAMPLE 2

CHARACTERISATION OF NT-RECA

In order to determine whether fusion of the nuclear localisation signal had any influence on the biochemical properties of RecA, a number of reactions were tested: (I) In *E. coli*, RecA confers UV resistance directly via recombinational repair of replication blocks and indirectly by mediating induction of SOS responses including increased expression of RecA itself (Roberts et al., 1978). To test the function of nt-RecA plasmid pEV/nt-recA, in which the nt-recA gene was transcribed from the phage λP$_l$ promoter, was introduced into the *E.coli* RecA- strain DH5α.

In particular, plasmid pEV/nt-recA was transformed into *E. coli* strain DH5α (supE44, ΔlacU169(Φ80lacZΔM15), hsdR17, recA1, endA1, gyrA96, thi-1, relA1, Gibco/BRL) which harboured a plasmid named 537 (Strebel et al., 1986) encoding a heat inducible lambda repressor gene. Cultures were grown at 28° C. in LB medium supplemented with ampicillin (100 μg/ml) and kanamycin (25 μ/ml). Expression was induced by a temperature shift to 42° C. After an additional 2 hour growth and expression period, the cells were harvested by centrifugation and washed in 250 mM Tris/HCl pH7.5, 25% (w/v) sucrose. High levels of expression, by thermal inactivation of the λcI857 repressor, turned out to be lethal. However, the cells were viable and UV-tolerant at 28 ° C., indicating that nt-RecA was functional. Purification of nt-RecA was as described for RecA by Cox et al. (1981) with the modifications of Griffith and Shores (1985), yielding 20 mg nt-RecA from 2 g of cells. The protein was stored in 20 mM Tris/HCl pH7.5, 1 mM EDTA, 1 mM DTT buffer containing 20% (v/v) glycerol at −20° C. The protein concentration was determined according to Bradford (1976). The purity and identity of nt-RecA protein was verified by SDS polyacrylamide gelelectrophoresis, Coomassie Blue staining, and Western blotting using antibody ARM414, an antibody produced according to conventional procedures.

The preparation contained a single protein visible in the Coomassie Blue stain. This protein reacted with the anti-RecA antibody in the Western blot. Using these criteria, the nt-RecA preparation was of equal purity with a preparation of RecA protein which had been purified according to the same protocol from a nalidixic-acid-induced *E. coli* cells harbouring plasmid pDR1453. (II) ATPase, ssDNA binding, and strand-exchange activities were analysed with highly purified nt-RecA protein produced by heat induction of a recAl *E. coli* strain carrying pEV/nt-recA. Purified nt-RecA preparations were shown to contain small amounts (less than 5%) of a protein of the molecular weight of authentic RecA presumably resulting from processing by an unspecific protease or from translation starting at an internal initiation codon in nt-recA.

Figure 2:
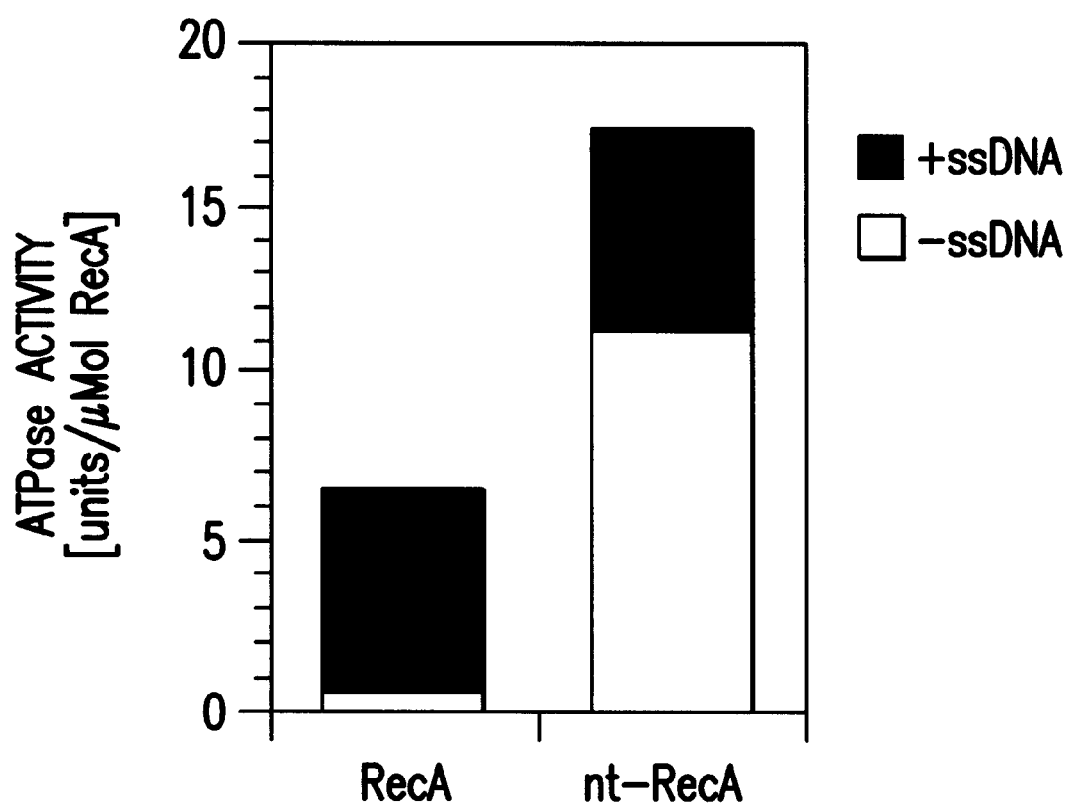
Figure 3:
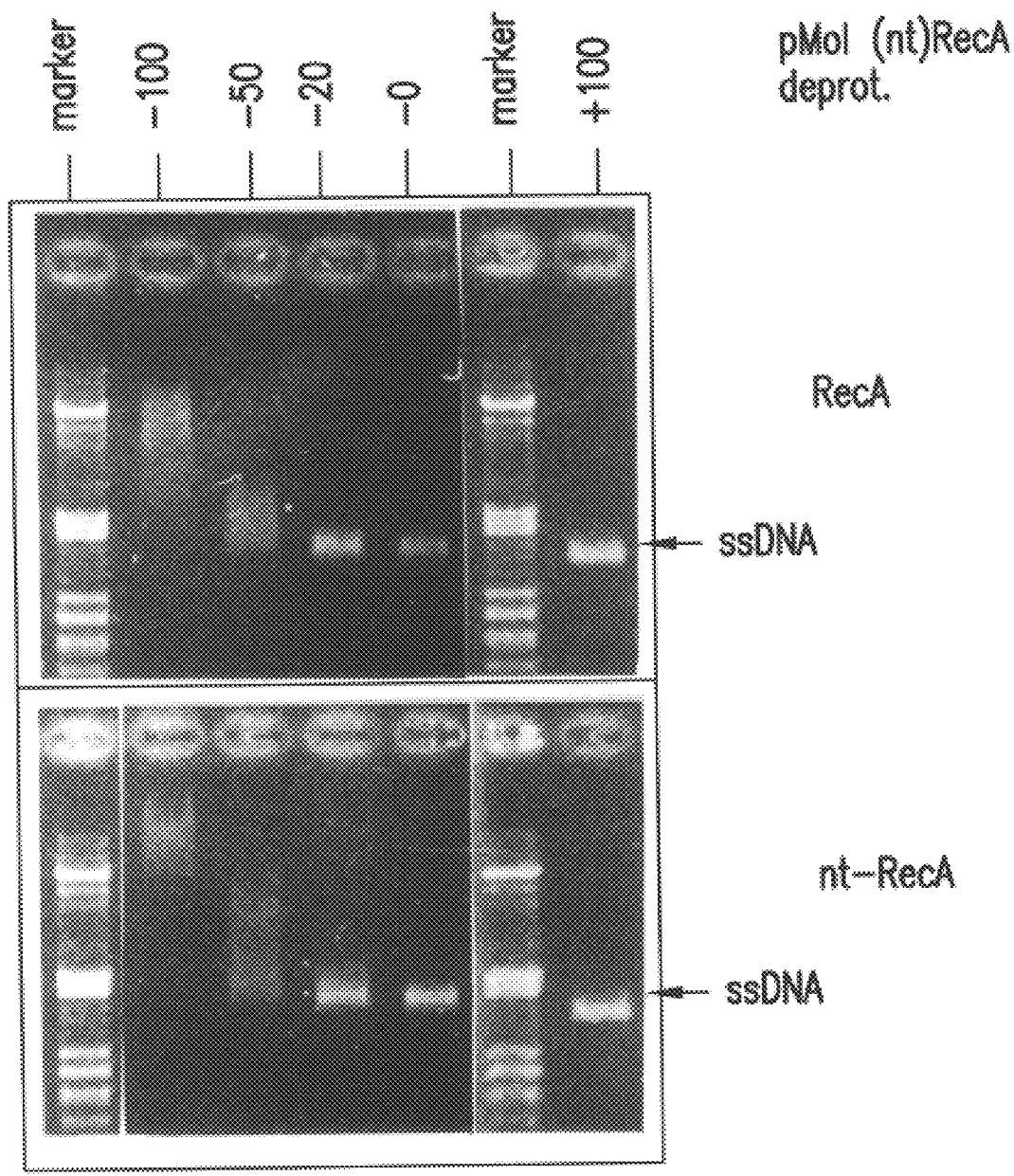
Figure 4:
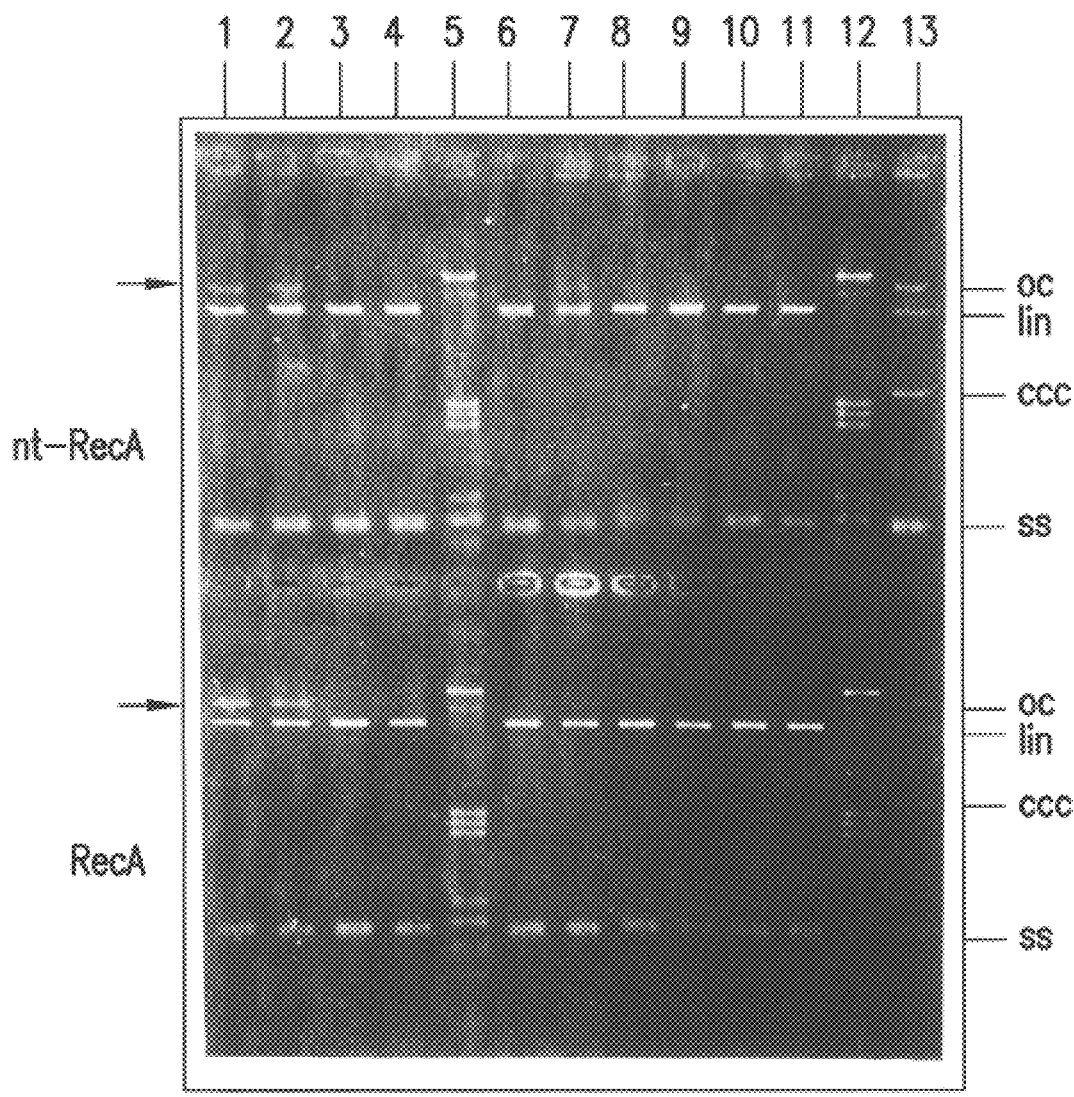

The ATPase activities of nt-RecA and authentic RecA, both purified from *E. coli* cultures by the same procedure (Griffith and Shores, 1985), were assayed in parallel in the presence and absence of ssDNA (Shibata et al., 1981). Essentially, ATPase activity was determined as described by Shibata et al. (1981) except that [$^3$H]ATP was substituted by [$^{14}$C]ATP (Amersham, specific activity 5×10$^{12}$ Ci/Mol). The basal ATPase activity of authentic RecA was found to be low but to be stimulated 20-fold by the addition of ssDNA, as expected (see Roca and Cox, 1990). In contrast, the basal ATPase activity of nt-RecA was found to be much higher and stimulated proportionally less by the addition of ssDNA (FIG. 2). (III) Binding of purified nt-RecA to ssDNA was assayed using gel retardation assays. A fixed quantity of ssDNA was incubated with increasing amounts of purified RecA and nt-RecA protein in the presence of ySATP to prevent dissociation of the complexes. In particular, binding of nt-RecA and RecA to ssDNA was determined in a total volume of 20 μl 25 mM Tris/acetate, 4 mM MgCl$_2$, 1 mM DTT, 20 μM nucleotide ssDNA from a derivative of phage M13mp18, described by Wada et al. (1994), and 2 m μ γSATP. Different quantities of protein (0, 20, 50, and 100 pMol) were incubated for 30 min at 37° C. with this mixture. For deproteinisation, SDS and EDTA were added to final concentrations of 1% (w/v) and 10 mM, respectively (Riddles and Lehmann, 1985). No differences in binding kinetics were observed (FIG. 3). (IV) RecA and nt-RecA proteins promoted strand-exchange between linear dsDNA and circular ssDNA (Menetski et al., 1990) with the same kinetics (FIG. 4). The strand-exchange reaction was performed exactly as described by Menetski et al. (1990). Closed circular ssDNA and BglI linearised dsDNA prepared from a derivative of phage M13mp18 (Wada et al., 1994) were used as substrates. These tests therefore indicated that nt-RecA exhibited the activities expected of a RecA protein.

EXAMPLE 3

CHARACTERISATION OF RECA AND NT-RECA TRANSGENIC PLANTS

Agrobacteria harbouring binary vectors carrying the recA and nt-recA transgenes were used to infect tobacco leaf disks: Plasmids pS/recA and pS/nt-recA were transferred to Agrobacterium tumefaciens strain GV3101/pMP90RK (Koncz and Schell, 1986) via electroporation, and the resulting strains (plants transgenic for recA were designated G64 and the nt-recA transgenic plants G63) used to inoculate leaf disks made from sterile tobacco SR1 plants according to published procedures (Koncz and Schell, 1986). Transformed shoots were selected on sulfadiazine (100 mg/l). Plants were regenerated and tested for rooting on sulfadiazine (100 mg/l). Transgenic plants were grown to maturity in the green house and seeds harvested. The inheritance of the transgenes was tested by germination of seeds in the presence of sulfadiazine on the same media. SR1hph2 plants were grown from seedlings which were selected on hygromycin (15 mg/l) under sterile conditions. G63 and G64 plants were crossed to SR1hph2 plants in the green house. Siblings harbouring the recA and hph2 transgenes were selected by growth of seedlings in the presence of both sulfadiazine (100 mg/l) and hygromycin (15 mg/l) under sterile conditions. Plants were grown to maturity without further selection. Individual transgenic plants were numbered consecutively. Shoots which rooted on selective media containing sulfonamide were considered to be resistant and were selected for further analysis.

The presence of recA transgenes was confirmed by Southern blots. For Southern hybridisations, total DNA prepared from leaves (Murray and Thompson, 1980) was restricted with EcoRI, and the fragments separated by agarose gel electrophoresis and blotted to a Nylon membrane (Zetaprobe, Biorad). The membrane was hybridised according to the manufacturers guidelines, to radioactively labeled probes prepared as described by Feinberg and Vogelstein (1984). Fragments encoding recA sequences were detected using a fragment from pRecA-4 which covered the entire gene. The copy number of inserts was determined using probes specific for border fragments which were derived from the Sulr. and recA genes. It was found that 11 of 12 sulfonamide resistant G64 plants carried an intact recA transgene. Plants with single copy inserts were selected and shown to transmit the sulfonamide resistance marker to their progeny as a single Mendelian trait. In contrast, only three of 36 G63 plants were found to carry an intact nt-recA gene. In one of them, G63/19, the right border of the T-DNA was deleted. The deletion resulted in a fusion of the 35S promoter sequences controlling nt-recA expression to plant genomic sequences. Other transgenic plant lines harboured either no recA sequences or had rearranged nt-recA genes. The intact nt-recA transgenes in the three independent transgenic plants were shown to be present in single copy and to be inherited as a single Mendelian trait.

Figure 5:
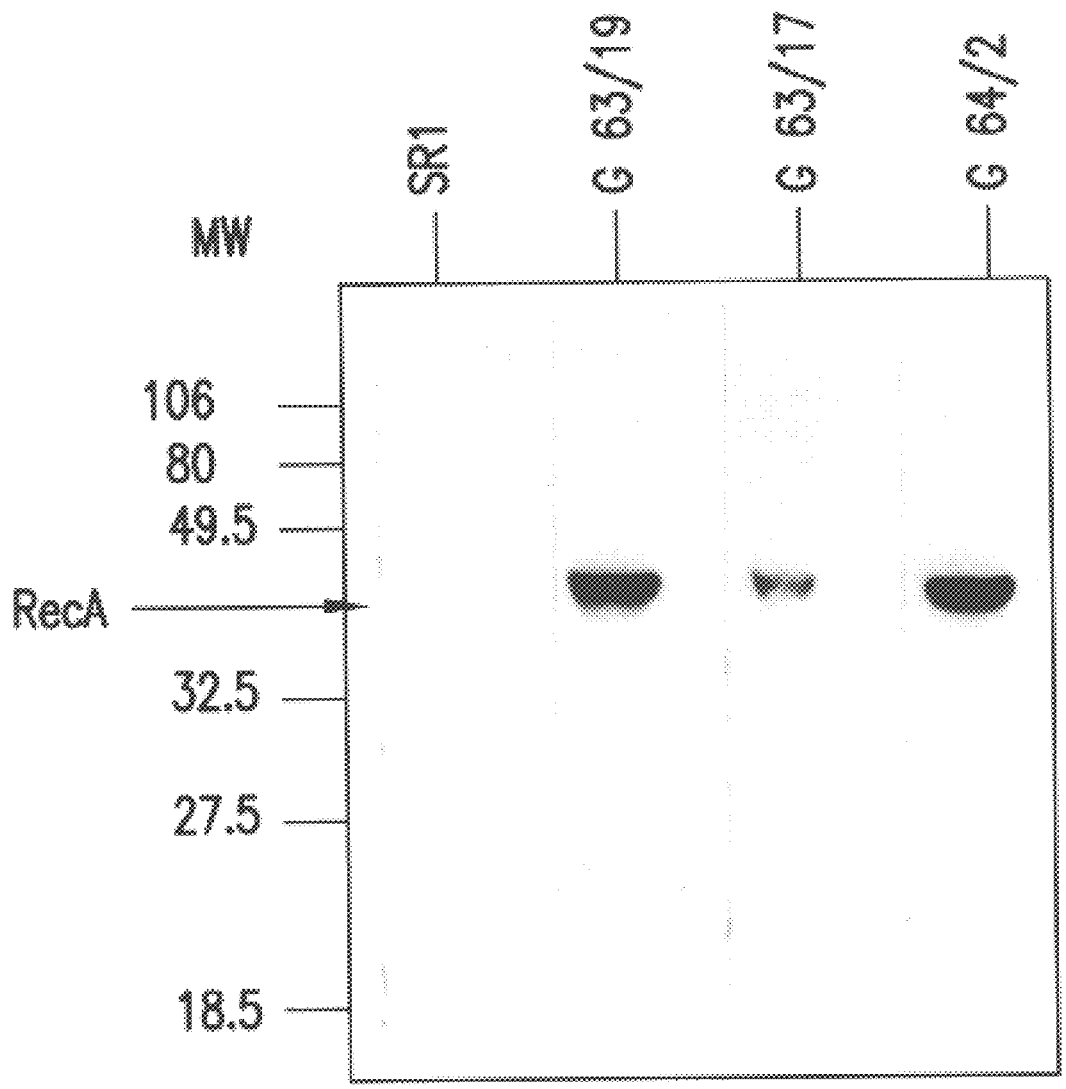

Expression of the recA and nt-recA genes was monitored using Western blots of protein extracts of leaves probed with a RecA-specific monoclonal mouse antibody (ARM414, Ikeda et al.,1990). First, proteins were extracted from leaves of plants grown in sterile culture. Leaves were ground with Laemmli sample buffer (Laemmli, 1970) (without bromphenol blue) plus sea sand, using a glass rod in an Eppendorf tube. After heat denaturation of the samples for 15 min at 95° C., the extract was cleared by centrifugation and the supernatant used for further analysis. The protein concentration was determined (Bradford, 1976) and 50 μg used for electrophoresis on polyacrylamide SDS gels according to Laemmli (1970). Proteins were transferred to nitrocellulose membranes (Schleicher and Schuell, pore size 0.45 μm) as described (Towbin, 1979). RecA protein was detected using the monoclonal anti-RecA antibody ARM414 (Ikeda et al., 1990) in a 1:200 dilution in TBST buffer after blocking of non-specific protein binding by 5% non-fat dry milk. A second antibody (goat anti-mouse, Promega) coupled to alkaline phosphatase and NBT/BCIP (Promega) staining or a second anti-mouse antibody coupled to horse radish peroxidase and chemiluminescence (ECL, Amersham) was used to develop the blot. All plants with an intact recA or nt-recA gene were thus shown to express RecA protein. Expression in G64 plants (recA) was similar in most transgenics and amounted to about 0.1% of total plant protein, as judged from a comparison of staining intensities with those of a dilution series of purified RecA protein. The expression level of nt-recA ranged from 0.01% (G63/17) to 0.1% (G63/19) of total protein. Both RecA and nt-RecA proteins appeared stable in plant cells and showed the expected molecular weights (FIG. 5). In nt-recA transgenic plants, small amounts of additional proteins were detected with the antibody. Since these proteins were of lower molecular weight, they presumably were degradation products of the actual nt-RecA protein.

The localisation of the RecA and nt-RecA proteins in the cell was studied by indirect immunbfluorescence. Plants with comparable expression levels were selected (G64/2 and G63/19) and protoplasts or root squashes were prepared. The preparation of protoplasts was done, according to the method of Negrutiu (1987), for immuno-histochemical localisation of RecA and nt-RecA protein. Proteins were fixed with 5% formaldehyde ($10^5$ protoplasts in 2 ml K3, 0.4M sucrose) at room temperature. Formaldeyde was removed by washing in W5 and chlorophyll extracted with methanol. Nonspecific binding was blocked by an incubation of the protoplast preparation in 5% BSA in TBST for 1 hour. The protoplasts were collected by centrifugation and incubated with anti-RecA antibody ARM414 (1:50) in TBST. After extensive washing with TBST buffer containing 5% BSA, the protoplasts were incubated with FITC-labelled anti-mouse antibody (Promega, 1:1000). Unbound antibody was removed by washing with TBST 5% BSA. Nuclei were stained with DAPI (2 μg/ml) in the same buffer. The preparation was examined using fluorescence microscopy (Zeiss Axiophot).

RecA and nt-RecA proteins were localised in whole tissue from young plants after fixation of leaves or roots in methanol:acetic acid (3:1) for 1 hour at room temperature. Tissue was equilibrated with K3 medium and incubated over night with 0.9% cellulase in the same medium. After incubation in acetic acid for 5 min, the tissue was transferred to a slide and squashed. Staining with anti-RecA antibody was as described above for protoplasts.

In G63/19 plants, FITC-fluorescence was found almost exclusively in the nucleus (FIG. 6). Some staining was visible also in the chloroplasts. In contrast, in G64/2 cells the nuclei were not particularly stained. However, there seemed to be a weak preference for association with the nucleus and concentration in the region around the nucleus (FIG. 6). Only background staining was observed in non-transgenic SR1 tobacco plants. It can be concluded that the SV40 nuclear localisation sequence in nt-RecA leads to efficient accumulation of this protein in the nucleus of the plant cell.

EXAMPLE 4

EXPRESSION OF RECA AND NT-RECA LEADS TO INCREASED RESISTANCE TO MITOMYCIN C

To analyse the effect of mitomycin C on plant growth, a quantitative and reproducible assay was used. The system described by Lebel et al. (1993) which allows to follow the fate of single plant cells was developed further to obtain greater sensitivity to mitomycin C and a monotonic survival-dose-response curve.

In this system protoplasts were prepared from sterile-grown tobacco SR1 plants and parallel preparations treated with various concentrations of mitomycin C. Subsequently the protoplasts were cultivated in a bead-type culture in the presence of mitomycin C. Untreated protoplasts actively divided and formed microcalli within a period of 4 to 8 weeks. The experimental details were as follows:

Protoplasts were prepared from leaves of axenically grown plants as described by Negrutiu (1987), with some modifications. Cut leaves (3 g) were digested in 50 ml K3, 0.4 M sucrose, 1 mg/l NAA, 0.2 mg/l kinetin, 0.6% cellulase Onozuka R10 (Serva), 0.3% Macerozyme R10 (Serva) in 145mm petri dishes at 22° C., in the dark, for 16 hours. Protoplasts were purified by filtration through steel sieves (250 µm and 100 µm mesh width) and washed once in W5 medium. Protoplasts were suspended in 1 ml of MaMg buffer (0.5 M mannitol, 15 mM $MgCl_2$, 0.1% MES, pH5.7), counted under a light microscope and diluted to a final concentration of $10^6$ cells/ml with K3, 0.4 M sucrose. A 1 ml aliquot of protoplast solution was diluted with 9 ml K3, 0.4 M sucrose medium and mitomycin C added from a stock solution, to the final concentrations indicated in FIG. 7. After incubation for 2 days in the dark at 22° C., the protoplasts were cultivated using the bead-type technique of Shillito et al. (1983) with some modifications. Protoplasts were embedded by dilution with an equal volume of media containing 0.8% low-melting-point agarose (FMC), as a gelling agent, and grown on a solid support carrier system (paper filter discs) in 20 ml liquid media. Cultures were grown for approximately 4 weeks with weekly changes of media. Survival was scored when the microcalli reached sizes of 2 to 4 mm. Plants were regenerated from representative samples. These plants showed no obvious growth abnormalities.

In a typical control experiment, 10% to 20% of the protoplasts plated grew to microcalli. Increasing concentrations of mitomycin C progressively inhibited the formation of microcalli (FIG. 7). No growth (less than $10^{-3}$% of control values) was observed at concentrations of 40 µ/ml and above. The survival curve showed a low-dose shoulder suggesting the presence of repair mechanisms leading to resistance to mitomycin C followed by a semi-logarithmic region at high doses of mitomycin C causing damage which can no longer be repaired by the endogenous repair mechanisms.

Protoplasts of a plant homozygous for the recA transgene (G64/2) were slightly but significantly more resistant to the toxic effect of mitomycin C than control cells. At concentrations of 40 µg/ml mitomycin C more than 0.1% of the cells survived and grew to microcalli (FIG. 7). However, no recA transgenic cells (less than $10^{-3}$% of control values) grew at mitomycin C concentrations of 50 µg/ml and above. In contrast, more than 0.1% nt-recA transgenic protoplasts (homozygous G63/19) were able to grow and regenerate at concentrations of up to 60 µ/ml mitomycin C, the highest concentration tested (FIG. 7).

EXAMPLE 5

INTRACHROMOSOMAL RECOMBINATION OF A CHROMOSOMAL MARKER IS STIMULATED BY RECA AND NT-RECA

Plants usually contain large amounts of repetitive DNA sequences. Recombination within these sequences apparently played a role in genome evolution (for review see: Flavell, 1982). To study the process of intrachromosomal recombination in plants, Peterhans et al. (1990) have developed a transgenic system. A pair of deletion derivatives of the selectable marker gene neomycin phosphotransferase (nptII, Beck et al., 1982) were stably integrated into the tobacco genome. The deletions removed portions of either the 5' or the 3' end of the gene rendering it non-functional. The segments in line SR1hph2 (Peterhans et al., 1990) were oriented as direct repeats with a 352-bp homologous overlap, interrupted by a functional hygromycin phosphotransferase gene (Van den Elzen et al., 1985). In this line, the basic module was present in three tightly linked copies in the genome. Intrachromosomal recombination events which lead to restoration of a functional nptII gene can easily be detected by selection of kanamycin resistant cells in tissue culture.

To study the influence of RecA and nt-RecA expression on intrachromosomal recombination, line SR1hph2 containing the defective nptII genes was crossed respectively to the homozygous lines G64/2 and G63/19. Progeny plants carrying the recA respectively nt-recA genes as well as the defective nptII genes were selected by germinating seeds on hygromycin and sulfonamide. Plants resistant to both antibiotics were grown under sterile culture conditions without further selection and leaf mesophyll protoplasts were prepared as described in Example 4. To determine the number of intrachromosomal recombination events, cultures were grown for 6 to 8 weeks in the presence of 100 µ/ml kanamycin after embedding. To determine the regeneration frequency, protoplasts were grown under identical conditions without kanamycin. From representative samples of microcalli, plants were regenerated to verify resistance to kanamycin. Protoplasts were plated and cultured until microcalli appeared. The number of protoplasts forming microcalli in the absence of selection (regeneration frequency) was determined for each batch of protoplasts and found to be about 20% to 30% for all protoplast preparations. The number of protoplasts regenerating in the presence of kanamycin was determined. The frequency of intrachromosomal recombination was calculated from the number of microcalli which grew on kanamycin versus the total number of calli appearing on non-selective media. 20 kanamycin-resistant microcalli were selected at random for regeneration into plants. All regenerated plants formed roots on kanamycin-containing medium, confirming that calli which grew in the presence of kanamycin were indeed resistant to the antibiotic.

The frequency of intrachromosomal recombination was found to be $1.04 \times 10^{-5}$ in the control line SR1hph2. In contrast, the frequencies in G64/2 X SR1hph2 and G63/19 X SR1hph2 were found to be $5.37 \times 10^{-5}$ and $10.3 \times 10^{-5}$, respectively (FIG. 8). These data show that the RecA protein, especially if targeted to the nucleus, is able to interact with the plant chromosome and the host recombination machinery and to markedly increase the level of intrachromosomal somatic recombination.

EXAMPLE 6

ENHANCEMENT OF GENE TARGETING FREQUENCIES IN PLANTS BY ECTOPIC NT-RECA EXPRESSION

A chimeric target locus was generated which consists of the seed specific high molecular weight glutenin (HMW) promoter (Colot et al., 1987) and additional sequences consisting of pBR322 and a selectable marker conferring methotrexate resistance in plants. To obtain this construct, the HMW promoter was cloned as an EcoRI/BamHI fragment into the binary vector pMN001 (Reiss et al., 1994). The resulting plasmid was transferred via electroporation to Agrobacterium (GV3101pMP90RK, Koncz and Schell, 1986) and the resulting strains were used to generate transgenic tobacco SR1 plants by leaf disk infection according to published methods (Marton et al., 1982; De Block et al., 1984; Marton, 1984; Horsch et al., 1985). These plants were characterized by Southern blotting and one line which contained the chimeric target locus in single copy designated B18/4. This line expressed NPT II in seeds, but no activity was detected in leaves using a sensitive enzymatic assay (Reiss et al., 1984). When callus was induced on leaf disks from these plants, green living material readily developed on methotrexate, but no callus formed on kanamycin. These plants were crossed to G63/19 SR1 plants expressing the nt-RecA protein (Reiss et al., 1996).

A repair construct was made which would lead to constitutive expression of NPT II upon homologous recombination with the B18/4 target. This construct was identical to the one used to generate B18/4, but contained a promoter expressed in all tissues, the CaMV 35S promoter, inserted into the BamHI site between the HMW promoter and the npt II gene and the npt II gene was the non-functional variant D42 which contained a carboxyterminal deletion shown to yield no active protein in *E. coli* (Beck et al., 1982). This plasmid was introduced into Agrobacterium (GV3101pMP90RK) as described above to yield strain G125.

To analyze gene targeting, siblings obtained from G63/19 plants crossed to B18/4 were selected on methotrexate and sulfonamide to select for the presence of both sets of transgenes. Leaf disks were prepared and transformed with Agrobacterium strain G125 which harboured the repair construct. In control transformations, 500 calli were obtained with G125 on a total of 58 SR1 leaf disks after selection on methotrexate. This demonstrated that G125 was fully functional. In total, 189 leaf disks from B18/4×G63/19 were infected with G125 and 21 kanamycin resistance calli obtained after selection on kanamycin.

To determine whether the resistant calli derived from potential gene targeting events, total genomic DNA was prepared from 9 of them. The DNA was amplified by PCR with a primer pair specific for an intact npt II gene under 35S promoter control (Primer 1 homologous to the −90 region of the 35S promoter: 5'GTG GAT TGA TGT GAT ATC TCC3' (SEQ ID NO: 3); Primer 2 homologous to sequences of npt II deleted in D42: 5'CCG CTC AGA AGA ACT CGT CA3' (SEQ ID NO: 4)). A fragment of the size predicted for amplification of the restored nptII gene with this primer pair was obtained in six calli. No amplification product was obtained with DNA from the parental B18/4 line and the residual 3 calli. These results indicate the presence of an intact npt II gene under 35S promoter control in 6 of the 9 calli investigated. The npt II gene in the 3 kanamycin resistant, but PCR negative calli most likely was activated by somaclonal variation, not by gene targeting.

The frequency of restoration of an intact npt II gene expressed in leaf tissue by transformation with G125 can be calculated therefore as follows:

The transformation frequency in the control experiment was 500 transformants per 58 leaf disks or 8.6/leaf disk. Thus, it was to be expected that in a total of 189 B18/4× G63/19 leaf disks transformed, approximately 189×8,6= 1625 transformants were generated without selection on kanamycin. A number of 21 kanamycin resistant calli was detected. Therefore, these calli appeared with a frequency of 21/1625 which approximately equals 1.3%. In a representative sample of 9, 6 contained a restored npt II gene. Therefore the frequency of targeting in this experiment was 0.87%.

Transgenic target loci similar to the system described here were used previously. The targeting frequencies observed with those target loci using Agrobacterium-mediated transformation were in the order of $10^{-4}$ (Offringa et al., 1990). Although these experiments might not be directly comparable, the large increase in frequencies observed in our experiments indicate a stimulatory role of RecA expression.

REFERENCES

Beck, E., Ludwig, G., Auerswald, E. A., Reiss, B., and Schaller, H. (1982). Nucleotide sequence and exact localisation of the neomycin phosphotransferase gene from transposon Tn5. Gene 19, 327–336.

Borowy-Borowski, H., Lipman, R., and Tomasz, M. (1990). Recognition between mitomycin C and specific DNA sequences for cross-link formation. Biochemistry 29, 2999–3006.

Bradford, M. (1976). A rapid and sensitive method for the quantitation of microgram quantities of protein utilizing the principle of protein-dye binding. Analytical Biochemistry 72, 248–254.

Cashmore, A., Eds.Kosuge, T., Meredith, C. P., and Hollaender, A. (1983). Nuclear genes encoding the small-subunit of ribulose-1,5-bisphosphate carboxylase, in Genetic engineering of plants: An agricultural perspective. Plenum Press,New York 29–38.

Cerutti, H., Johnson, A. M., Boynton, J. E., Gillham, N. W. (1995). Inhibition of chloroplast DNA recombination and repair by dominant negative mutants of *Escherichia coli* RecA. Mol. Cell. Biology, 3003–3011.

Colot, V., Robert, L. S., Kavanagh, T. A., Bevan, M. W., and Thompson, R. D. (1987). Localisation of sequences in wheat endosperm protein genes which confer tissue-specific expression in tobacco. EMBO J. 6, 3559–3564.

Cox, M. M., McEntee, K., and Lehman, I. R. (1981). A simple and rapid procedure for the large scale purification of the recA protein of *Escherichia coli*. J. Bio. Chem. 256, 4676–4678.

Crowl, R., Seamans, C., Lomedico, P., and McAndrew, St. (1985). Versatile expression vectors for high-level synthesis of cloned gene products in *Escherichia coli*. Gene 38, 31–38.

De Block, M., Herrera-Estrella, L., Van Montagu, M., Schell, J., and Zambryski, P. (1984). Expression of foreign genes in regenerated plants and in their progeny. EMBO J. 3, 1681–1690.

Dingwall, C. and Laskey, R A. (1986). Protein import into the cell nucleus. Annual Review of Cell Biology 2, 367–390.

Dunderdale, H J. and West, S C. (1994). Recombination genes and proteins. Current Opinion in Genetics and Development 4, 221–228.

Feinberg, A. and Vogelstein, B. (1984). A technique for radiolabeling DNA restriction endonuclease fragments to high specific activity. Analytical Biochemistry 137, 266–267.

Flavell, R. B. (1982). Sequence amplification, deletion and rearrangement: Major sources of variation during species divergence. In Genome Evolution. Dover,G. A. and Flavell,R. B. (eds), Academic Press, London 301–323.

Friedberg, E. C., (1985) DNA Repair. W.H. Freeman&Co., New York.

Griffith, J. and Shores, C. (1985). RecA protein rapidly crystallizes in the presence of spermidine: A valuable step in its purification and physical characterization. Biochem 24, 158–162.

Guerineau, F., Brooks, L., Meadows, J., Lucy, A., Robinson, C., and Mullineaux, P. (1990). Sulfonamide resistance gene for plant transformation. Plant Molecular Biology 15, 127–136.

Holliday, R. (1964). The induction of mitotic recombination by mitomycin C in Ustilago and Saccharomyces. Genetics 50, 323–335.

Horsch, R. B., Fry, J. E., Hoffman, N. L., Eichholz, D., Rogers, S. G., and Fraley, R. T. (1985). A simple and general method for transferring genes into plants. Science 227, 1229–1231.

Ikeda, M., Makino, O., and Shibata, T. (1990). Epitopes and active sites of the RecA protein. J. Biological Chemestry 265, 8948–8956.

Iyer, V. and Szybalski, W. (1963.). A molecular mechanism of mitomycin action: Linking of complementary DNA strands. Proc. Natl. Acad. Sci. USA 50, 355–362.

Kalderon, D., Roberts, B. L., Richardson, W. D., and Smith, A. E. (1984). A short amino acid sequence able to specify, nuclear location. Cell 39, 499–509.

Kido, M., Yoshihiro, Y., Nakanishi, M., Uchida, T., Okada, Y. (1992). *Eschiria coli* RecA protein modified with a nuclear location signal binds to chromosomes in living mammalian cells. Experimental Cell Research 198, 107–114.

Koncz, C. and Schell, J. (1986). The promoter of Tl-DNA gene 5 controls the tissue-specific expression of chimaeric genes carried by a novel type of Agrobacterium binary vector. Mol. Gen. Genet. 204, 383–396.

Kowalczykowski, S C. and Eggelston, A K. (1994). Homologous pairing and DNA strand-exchange proteins. Annual Review of Biochemistry 63, 991–1043.

Laemmli, U. K. (1970). Cleavage of structural proteins during the assembly of the head of the bacteriophage T4. Nature 227, 680–685.

Lebel, E G., Masson, J, Bogucki, A, and Paszkowski, J (1993). Stress-induced intrachromosomal recombination in plant somatic cells. Proc. Natl. Acad. Sci. USA 90, 422–426.

Marton, L., Wullems, G. J., Molendijk, L., and Schilperoort, R. A. (1982). In vitro transformation of cultured cells from Nicotiana tabacum by Agrobacterium tumefaciens. Nature 277, 129–131.

Marton, L. (1984), In Vasil I. K. (Ed.) Cell culture and somatic cell genetics in plants. Vol1. Academic Press, New York, 414–521.

Menetski, J P., Bear, D G., and Kowalczykowski, S C. (1990). Stable DNA heteroduplex formation catalyzed by the *Escherichia coli* RecA protein in the absence of ATP hydrolysis. Proc. Natl. Acad. Science USA 87, 21–25.

Murray, M. G. and Thompson, W. F. (1980). Rapid isolation of high molecular weight plant DNA. NAR 8, 4321–4325.

Negrutiu, I., Shillito, R., Potrykus, I., Biasini, G., and Sala, F. (1987). Hybrid genes in the analysis of transformation conditions. Plant Molecular Biology 8, 363–373.

Offringa, R., deGroot, M. J. A., Haagsman, H. J., Does, M. P., van den Elzen, P. J. M., and Hooykaas, P. J. J. (1990). Extrachromosomal homologous recombination and gene targeting in plant cells after Agrobacterium mediated transformation. EMBO J. 9, 3077–3084.

Ogawa, T., Yu, X., Shinohara, A., and Egelman, E. H. (1993). Similarity of the yeast RAD51 filament to the bacterial RecA filament. Science 259, 1896–1899.

Peterhans, A, Schlüpmann, H, Basse, C, and Paszkowski, J (1990). Intrachromosomal recombination in plants. EMBO J. 9, 3437–3445.

Pietrzak, M., Shillito, R. D., Hohn, T., and Potrykus, I. (1986). Expression in plants of two bacterial antibiotic resistance genes after protoplast transformation with a new plant expression vector. Nucl. Acids Res. 14, 5857–5869.

Reiss, B., Sprengel, R., and Schaller, H. (1984a). Protein fusions with the kanamycin resistance gene from transposon Tn5. EMBO J. 3, 3317–3322.

Reiss, B., Sprengel, R., Will, H., and Schaller, H. (1984b). A new sensitive method for qualitative and quantitative assay of neomycin phosphotransferase in crude cell extract. Gene 30, 211–218.

Reiss, B., Koncz, C., Moore, I., and Schell, J. (1994). A family of binary gene vectors with low inter-transformant variation. Plant Physiology (Life Sci. Adv. ) 13, 143–149.

Reiss, B., Klemm, M., Kosak, H., and Schell, J. (1996). RecA protein stimulates homologous recombination in plants. Proc. Natl. Acad. Sci. USA, 93, 3094–3098.

Riddles, P. W. and Lehmann, I. R. (1985). The formation of plectonemic joints by the recA protein of *Escherichia coli*. Requirement for ATP hydrolysis. Journal of Biological Chemistry 260, 170–173.

Roberts, J. W., Roberts, C. W., and Craig, N. L. (1978). *Escherichia coli* recA gene product inactivates phage lambda repressor. Proc. Natl. Acad. Sci. USA 75, 4714–4718.

Roca, A. and Cox, M. (1990). The RecA protein: Structure and function. Critical Reviews in Biochemistry and Molecular Biology 25, 415–456.

Rupp, W. D., Howard-Flanders, P. (1968) Discontinuities in the DNA synthesised in an excision-defective strain of *Escherichia coli* following ultraviolet irradiation. J. Mol. Biol. 31, 291–304.

Shaw, M. and Cohen, M. (1964). Chromosome exchanges in human leukocytes induced by mitomycin C. Genetics 51, 181–190.

Sancar, A. and Rupp, W. D. (1979). Physical map of the recA gene. Proc. Natl. Acad. Sci. USA 76, 3144–3148.

Shibata, T., Cunningham, R. C., and Radding, Ch. M. (1981). Homologous pairing in genetic recombination. Journal of Biological Chemistry 256, 7557–7564.

Shillito, R. D., Paszkowski, J., and Potrykus, I. (1983). Agarose plating and a bead type culture technique enable and stimulate development of protoplast-derived colonies in a number of plant species. Plant Cell Reports 2, 244–247.

Shinohara, A., Ogawa, H., and Ogawa, T. (1992). Rad51 protein involved in repair and recombination in S. cerevisiae is a RecA-like protein. Cell 69, 457–470.

Silver, P. A. (1991). How proteins enter the nucleus. Cell 64, 489–497.

Sinden, R. R., Cole R. S. (1978) Repair of cross-linked DNA and survival of *Escherichia coli* treated with psoralen and light: effects of mutations influencing genetic recombination and DNA metabolism. J. Bacteriol. 136, 538–547.

Spivak, I. M., Kostetsky, I. E., Shpielevaya, S. P., Kordyum, V. A., Zhestyanikov, V. D. (1991). Caffeine-induced reduction of the survival of -irradiated HeLa cells and the reversal of the caffeine effect by *Escherichia coli* RecA protein. Mutation Research, 246, 103–107.

Strebel, K., Beck, E., Strohmaier, K., and Schaller, H. (1986). Characterization of foot-and-mouth disease virus gene products with antisera against bacterially synthesized fusion proteins. Journal of Virology 57, 983–991.

Sung, P. (1994). Catalysis of ATP-dependent homologous DNA pairing and strand exchange by yeast RAD51 protein. Science 265, 1241–1243.

Suzuki, D. T. (1965). Effects of mitomycin C on crossing over in drosophila melanogaster. Genetics 51, 635–640.

Terasawa, M., Shinohara, A., Hotta, Y., Ogawa, H., and Ogawa, T. (1995). Localization of RecA-like recombination proteins on chromosomes of the lily at various meiotic stages. Genes & Development 9, 925–934.

Towbin, H., Stachelin, T., and Gordon, J. (1979). Electrophoretic transfer of proteins from polyacrylamide gels to nitrocellulose sheets: procedure and some applications. Proc. Natl. Acad. Sci. USA 76, 4340–4354.

van den Elzen, P., Townsend, J., Lee, K. Y., and Bedbrook, J. R. (1985). A chimeric hygromycin resistance gene as a selectable marker in plant cells. Plant Molecular Biology 5, 299–302.

Wada, M., Klein, Ch., Schell, J., and Reiss, B. (1994). A functional assay for Taq DNA polymerase in PCR. Biotechniques 16, 26–30.

Wang, Y., Maher, V., Liskay, R., and McCormick, J. (1988). Carcinogens can induce homologous recombination between duplicated chromosomal sequences in mouse L cells. Mol. Cell. Biol. 8, 196–202.

Wassmann, C. C., Reiss, B., Bartlett, S. G., and Bohnert, H. J. (1986). The importance of the transit peptide and the transported protein for protein import into chloroplasts. Mol. Gen. Genet. 205, 446–453.

Witkin, E. M., McCall, J. O., Volkert, M. R., Wermundsen, I. E. (1982) Constitutive expression of SOS functions and modulation of mutagenesis resulting from resolution of genetic instability at ornear the recA locus of *Escherichia coli*. Mol. Gen. Genet. 185, 43–50.

What is claimed is:

1. A method for the production of a transgenic plant or a transgenic plant cell with enhanced recombination, comprising
   (1) insertion of at least a first and second DNA sequence into the genome of said plant or plant cell, said first DNA comprising
      (a) the sequence of at least one gene of interest, and
      (b) a sequence which encodes a selection marker expressible in said plant or plant cell, and
   said second DNA comprising a sequence that encodes a RecA operatively linked to a DNA sequence encoding a nuclear targeting sequence for promoting homologous recombination, and
   (2) selection of transgenic plants or plant cells which have taken up said DNA, and
   (3) culturing of said transgenic plant or transgenic plant cells in a suitable culture medium.

2. The method according to claim 1, wherein said transgenic plant or transgenic plant cell is *Nicotiana tabacum* or *Arabidopsis thaliana*.

3. A method for the production of a transgenic plant or a transgenic plant cell with enhanced recombination, comprising
   (1) insertion of DNA into the genome of a plant or plant cell, said DNA comprising
      (a) the sequence of at least one gene of interest, and
      (b) a sequence which encodes a selection marker expressible in said plant or plant cell, and
      (c) a nucleic acid molecule encoding the amino acid sequence of the *E. coli* RecA protein,
   wherein said nucleic acid molecule is operatively linked to a DNA sequence encoding a nuclear targeting sequence,
   (2) selection of desired transgenic plants or transgenic plant cells which have taken up said DNA, and
   (3) culturing of said desired transgenic plants or transgenic plant cells in a suitable culture medium.

4. The method according to claim 1 or 3, wherein said selection marker is Hyg$^R$, Km$^R$, PPT$^R$, Mtx$^R$ or Sul$^R$.

5. A transgenic plant or transgenic plant cell prepared by the method of claim 1.

6. A vector which comprises a DNA sequence encoding a nuclear targeting sequence operatively linked to a sequence that encodes a RecA and further comprising a DNA sequence encoding a selectable marker.

7. A vector which comprises a DNA sequence encoding a T SV40 nuclear targeting sequence operatively linked to a sequence that encodes a RecA and further comprising a DNA sequence encoding a selection marker and the DNA sequence of at least one gene of interest.

8. The method of claim 1 or 3, wherein said nuclear targeting sequence is that of T SV40.

9. The method according to claim 1, wherein said nucleic acid molecule encodes *E. coli* RecA.

10. The method according to claim 1 or 3, wherein said insertion is mediated via a member selected from the group consisting of PEG transformation, Agrobacterium transformation, electroporation, particle bombardment, liposome fusion, in planta transformation, calcium phosphate precipitation and virus infection.

11. A method for the production of a transgenic plant or a transgenic plant cell with enhanced recombination, comprising
    (1) insertion of DNA into the genome of a plant or plant cell, said DNA comprising
        (a) the sequence of at least one gene of interest, and
        (b) a sequence which encodes a selection marker expressible in said plant or plant cell, and
        (c) a nucleic acid molecule encoding the amino acid sequence of the *E. coli* RecA protein,
    and wherein said nucleic acid molecule of (c) is operatively linked to a DNA sequence encoding the T SV40 nuclear targeting sequence,
    (2) selection of desired transgenic plants or transgenic plant cells which have taken up said DNA, and
    (3) culturing of said desired transgenic plants or transgenic cells in a suitable culture medium.

12. The method according to claim 11, wherein said insertion is mediated via a member selected from the group consisting of PEG transformation, Agrobactenum transformation, electroporation, particle bombardment, liposome fusion, in planta transformation, calcium phosphate precipitation and virus infection.

13. A vector which comprises a DNA sequence encoding a T SV40 nuclear targeting sequence operatively linked to a
    a nucleic acid sequence encoding the amino acid sequence of the *E. coli* RecA protein,
wherein said vector further comprises a promoter that functions in plants, said promoter operably linked to said DNA sequence.

14. The vector according to claim 13, further comprising a DNA sequence encoding a selection marker.

15. The vector according to claim 13, further comprising at least one gene of interest.

16. A vector which comprises a DNA sequence encoding a T SV40 nuclear targeting sequence operatively linked to a sequence that encodes RecA that mediates strand-exchange and further comprising a DNA sequence encoding a selection marker and the DNA sequence of at least one gene of interest.

17. The vector according to claim 6, wherein said nuclear targeting sequence is the T SV40 nuclear targeting sequence or the RecA is the *E. coli* RecA protein.

18. The vector according to claim 7, wherein the RecA is the *E. coli* RecA protein.

19. The vector according to claim 17 or 18, wherein said vector is pS/nt-RecA or pEV/nt-RecA.

20. The method according to claim 9, wherein said nuclear targeting sequence is that of T SV40.

* * * * *